(12) United States Patent
Bellmann et al.

(10) Patent No.: US 6,610,318 B1
(45) Date of Patent: Aug. 26, 2003

(54) STERILE OPHTHALMOLOGICAL GEL PREPARATION APPLICABLE IN DROPS AND PROCESS FOR PRODUCING IT

(75) Inventors: Gunther Bellmann, Berlin (DE); Gudrun Claus-Herz, Berlin (DE); Cornelia Reimer Hevia, Berlin (DE)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 08/930,239

(22) PCT Filed: Feb. 20, 1996

(86) PCT No.: PCT/EP96/00697

§ 371 (c)(1),
(2), (4) Date: Jan. 11, 1999

(87) PCT Pub. No.: WO96/29984

PCT Pub. Date: Oct. 3, 1996

(30) Foreign Application Priority Data

Mar. 28, 1995 (DE) .......................... 195 11 322

(51) Int. Cl.$^7$ .............................. A61K 9/00; A61K 9/08; A61K 9/10
(52) U.S. Cl. ...................... 424/427; 424/428; 424/429; 424/400; 424/401
(58) Field of Search ................. 424/427, 429, 424/437, 428, 400, 401

(56) References Cited

U.S. PATENT DOCUMENTS

| | | | |
|---|---|---|---|
| 4,421,748 A | 12/1983 | Trager et al. ............... | 424/199 |
| 4,866,049 A | 9/1989 | Maumenee et al. ......... | 514/169 |
| 4,914,088 A | 4/1990 | Glonek et al. ................ | 514/76 |
| 5,032,392 A * | 7/1991 | Varma .......................... | 424/78 |
| 5,252,318 A * | 10/1993 | Joshi et al. .............. | 424/78.04 |
| 5,441,732 A | 8/1995 | Hoeg et al. ............... | 424/78.04 |
| 5,496,811 A | 3/1996 | Aviv et al. ..................... | 514/78 |

FOREIGN PATENT DOCUMENTS

| | | |
|---|---|---|
| EP | 0028110 A2 * | 5/1981 |
| EP | 0063870 | 3/1982 |
| EP | 0063870 A2 * | 3/1982 |
| EP | 0 312 814 | 4/1989 |
| EP | 0 391 369 | 10/1990 |
| EP | 0 459 148 | 10/1992 |
| EP | 0376852 B1 * | 6/1993 |
| EP | 0694310 | 1/1996 |
| WO | WO 88/00824 | 2/1988 |
| WO | WO 93/01814 A1 * | 2/1993 |
| WO | WO 93/21901 | 11/1993 |
| WO | WO 94/05298 A1 * | 3/1994 |
| WO | WO 94/05298 | 3/1994 |
| WO | WO95/05163 A1 * | 2/1995 |

OTHER PUBLICATIONS

Rote List 1994, No. 67256, No. 67257, No. 67258 Pharmaceutics: The Science of Dosage Form Design, Michel E. Alton (Ed.), Churchill Livingston, Edinburgh, 1988, 275–277; 285.

* cited by examiner

Primary Examiner—Thurman K. Page
Assistant Examiner—Rachel M. Bennett
(74) Attorney, Agent, or Firm—John E. Thomas

(57) ABSTRACT

The invention relates to a sterile ophthalmic drop preparation, especially a gel preparation, which comprises a two-phase carrier liquid or gel basis comprising a liquid aqueous and a liquid hydrophobic phase.

20 Claims, No Drawings

STERILE OPHTHALMOLOGICAL GEL PREPARATION APPLICABLE IN DROPS AND PROCESS FOR PRODUCING IT

This application is a 371 of PCT/EP96/00697 filed Feb. 20, 1996.

The invention relates to a sterile ophthalmic gel preparation that can be Applied in drop form, especially for use as an artificial tear fluid and for the treatment of "dry eye", as well as to a method for the production of such a gel preparation.

It has been known for some time to use aqueous preparations to replace natural tear fluid and to treat "dry eye", which aqueous preparations e.g. contain film-building materials based on polyvinylalcohol (PVOH), polyvinylpyrrolidone (PVP), cellulose derivatives or dextrane. An overview can e.g. be found in Sucker, Fuchs und Speiser, "Pharmazeutische Technologie" 1978. These are generally systems which only have one fluid or liquid phase, typically an aqueous solution of further components.

Where components are present which are difficult to dissolve in water or which are water-insoluble, these are suspended as solids, in finally divided form, in the aqueous phase.

In semisynthetic preparations, such as e.g. those based on cellulose derivatives or dextrane, production is made more difficult by the fact that such materials are difficult to obtain free of insoluble components. One therefore has to incur very high expenditure in preparing solutions from such preparations which do not lead to eye irritation caused by mechanical effects. Further, such preparations are very difficult to sterilize, since they can only with great difficulty, or not at all, be filtered to remove germs, and they can also not be autoclaved without deterioration in quality. Cellulose derivatives cannot be autoclaved without irreversible changes in viscosity. Dextrane preparations are partly decomposed by autoclaving.

Also polyvinylalcohol can only be sterilized by heating if a very pure hydrolized form is employed since otherwise the PVOH component is depolymerized. Since PVOH as well as PVP only provide relatively little thickening effect, rather high amounts of these components must be used to provide suitable viscosities. This leads to a very high load of the ophthalmological preparation with such materials, e.g. contents of more than 10% in the case of PVOH.

It is already known from DE 34 40 352 and DE 43 03 818, and also from U.S. Pat. No. 5,252,318, to use polyacrylic acid and its derivatives, such as e.g. Carbopole® 940 (obtainable from B. F. Goodrich Company) as the gel basis for sterile ophthalmic gel drop preparations. In U.S. Pat. No. 5,441,732, which was only published after the priority date of the instant application, a combination of two specific gel components is disclosed, one of which is gelled thermally, whereas the other is gelled by a change in pH. Various cellulose derivatives are described as the thermally reactive gel polymer, whereas polyacrylates, especially cross-linked polyadrylates, are mentioned as polymers gelling in dependance of the pH value. It appears that gel formation is intended to only occur in the eye, by the pH change after application to the eye. It is stated that these-polymer mixtures are to be used together with organic oils, wherein a multiplicity of active agents can be dissolved. Vitamine A is not mentioned.

With respect to compliance, non-irritation, shelf life etc., very high-standards must be met by ophthalmic preparations which are to be used as film-forming preparations or lubricating preparations. Especially where ophthalmic preparations must be used for any extended period of time, which e.g. is regularly the case in the treatment of "dry eye", even a temporary irritation, such as a burning sensation in the eye is an extremely unpleasant sensation, and is detrimental to any extended therapeutical treatment. It is self-understood that in the application of such ophthalmic preparations, impaired sight, blurred view or other acute irritations cannot be accepted.

In "dry eye" treatment, the use of vitamine A, generally in the form of vitamine A palmitate, has proven to be effective. Thus, gel drop preparations on Carbopol basis have been-commercialized (after the priority date of the instant application), which besides other customary components contain vitamine A palmitate. These are one-phase gels with a continuous aqueous liquid phase, and without any hydrophobic second liquid phase. These products have a shelf life of about a year, when the vitamine A component is provided in an excess of 40%. As trials have shown, the vitamine A content decreases by about 20% over six months in these preparations, so that at a 40% excess dosage, the guaranteed minimum content is still present after one year.

Natural tear fluid comprises inter alia a fatty component which comprises triglycerides and phospholipides. It has already been tried (WO 94/05298), to use triglycerides in synthetic tear liquids, which was, however, only possible when an emulgator was added, and the overall preparation was in the form of an emulsion, for topical application to the eye. This has the disadvantage that desirable residual amounts of natural tear fluid in the eye are destroyed by the emulgator component.

It is an important object of this invention-to provide ophthalmic preparations, especially gel preparations, which show an improved shelf life, especially when containing sensitive substances such as vitamine A and its derivatives.

It is a further important object of the invention to provide such preparations which do not cause acute irritations and impaired vision, especially when formulated for increased shelf life.

It is a further very important object of this invention to provide such preparations which make it possible to use the preparation repeatedly over an extended time period, and/or enable extended duration in the eye after each individual application without causing incompatibilities, lack of compliance, irritation to the eye and other such problems. The invention is based on various surprising findings.

On the one hand, it has surprisingly been found that relatively fast decomposition of vitamine A and its derivatives, especially vitamine A palmitate, in artificial tear fluids and preparations for "dry eye" treatment can be dramatically reduced when the preparation is in the form of a two component system with one aqueous liquid phase and one hydrophobic liquid phase. Especially it is preferred herein that the preparation-has a continuous aqueousphase wherein the hydrophobic liquid oil phase is provided in the form of very finely divided droplets. There is no easy explanation for this fact. Most probably, oxygen and/or light are responsible for the decomposition of vitamine A, and with respect to both, it should not make any material difference whether the preparation comprises one or two separate liquid phases. One would rather expect an increased, sensitivity with respect to oxygen and/or light in a solution of the vitamine A component in the hydrophobic phase.

Possibly, the simultaneous use of antioxidants, especially vitamine E and its derivatives and most specifically vitamine E acetate has an influence in these preparations. In any case, vitamine A is preferably used with such antioxidants in the inventive preparations.

On the other hand, a further surprising effect of the invention is that it makes it possible to prepare preparations with an aqueous and a liquid hydrophobic phase which come very close to the composition of natural tear liquid, and especially have a corresponding content of triglycerides, without any necessity of at the same time using emulgators. This is possible since according to the invention, such preparations are in the form of gel drop preparations. In contrast to preparations without any gel basis, triglycerides can be provided in the inventive gel preparations in the form of very finely divided droplets also over very extended storage periods, with the droplets being sufficiently stable in the gel even in the absence of any emulgator. It is possible without any problems to prepare such preparations so that they are sterile, and the preparations are not irritating and perfectly acceptable.

The inventive preparations, including gel preparations, have a refractive index which is almost completely the same as that of natural tear fluid. They provide extended duration and effect in the eye.

The inventive preparations appear to provide reduced surface tension of the aqueous eye gel, which leads to improved distribution on the cornea. Also, any active agent suspended or dissolved in the oil phase is more evenly distributed. wetability of objects to be placed on the cornea, such as contact lenses or the front: lenses of ophthalmological apparatuses, is improved.

Long term studies show that the inventive preparations are extremely stable in the 5 g polyfoil tube packages customary in trade, not only under the conditions of a temperate climate (29° C., 45% relative humidity), but also under conditions of the mediterranian/subtropical climate (26° C., 60% relative humidity) and even that of very hard and moist climates (31° C., 70% relative humidity) and show hardly any changes in vitamine A content (where provided), pH value, osmolality, viscosity and appearance.

Basically, those ophthalmologically acceptable organic oils are suitable as the liquid hydrophobic component of the inventive two-phase preparations, especially gels, which can be dispersed as droplets in an aqueous phase in the absence of emulgators. Examples are formed by fatty acid derivatives such as, especially, fatty acid esters, triglycerides and phthalic acid esters. Triglycerides are presently specifically preferred, especially the homogeneous or mixed triglycerides formed,mostly or totally from $C_8$–$C_{12}$ fatty acids. Especially, medium chain triglycerides of the type defined in "Deutsches Arzneibuch" (DAB) 10 (1993) are preferred. The acid component of these triglycerides is a mixture of at least 95% n-octanoic acid and n-decanoic acid; the remainder is formed by shorter chain fatty acids.

Such medium chain triglycerides are made semisynthetically from the oil of the dry solid part of the endosperm of cocos nucifera L., by hydrolizing the coco oil obtained from the endosperm, fractioning the thus obtained fatty acids, and re-esterification of the acids.

Such medium chain triglycerides are already in use as basic substances for cosmetics, as adjuvants and carriers for pharmaceuticals, and also for some foodstuffs. Very little is known, however, about their potential uses and the limits of such uses in ophthalmic preparations, although such medium chain triglycerides have very well known beneficial properties.

Inventive preparations, especially on gel basis, with typical contents between 0.1 and 3 weight-%, especially approximately 0.2 weight-% polyacrylic acid as the gel-forming agent in the aqueous phase, contain typically between 0.5 and 10 weight-%, especially approximately 1 weight-% of such medium chain triglycerides.

Inventive gel preparations preferably have a viscosity in the range of approximately 2000 to 6000 mPa·s, at a pH value between 6 and 8.

The inventive preparations preferably contain a preserving agent, such as especially centrimid, benzalkoniumchloride or thiomersal. It is further preferred that such gel preparations, contain at least one isotonic agent, for which purpose sorbitol is specifically suitable.

The especially preferred content of a vitamine A component, especially vitamine A palmitate, is of the order of 500 international units per gram of the inventive preparation. The vitamine A component is specifically preferred to be stabilized with a small amount of at least one antioxidant, wherein vitamins E and vitamine E acetate are specifically advantageous.

Production of an inventive sterile preparation, especially gel, proceeds in a multistep method. In preparing the gel, a sterile polyacrylic acid suspension is preferably obtained by the procedure disclosed in DE 43 03 818, i.e. by autoclaving at about 120° C., 1 bar excess pressure, and 20 minutes duration. In parallel, an aqueous solution is prepared which contains the preserving agent and the isotonic, i.e. preferably centrimid and sorbitol. This aqueous solution is added to the autoclaved polyacrylic acid suspension by sterile filtration, using nitrogen as the pressurizing gas, or, in case, more simply using pressurized air. Subsequently, careful neutralization is achieved by adding sterile sodiumhydroxide solution, which initiates gel formation. Once neutralization has been achieved, there is no free base any more in the forming gel. The hydrophobic liquid component, i.e. preferably the medium chain triglyceride component, is then worked into the sterile gel under antiseptic conditions. Stirring is maintained until complete homogenization has been achieved. In the inventive dispersion, the size of the thus obtained oil droplets is maximally about 100 $\mu$m and is otherwise of the kind, which is obtained in a conventional emulsion without the addition of strong emulgators.

The sterile gel can now be confectioned in the customary fashion.

Otherwise, an active agent such as especially vitamine A palmitate can be added to the thus formed sterile gel, in such a fashion that the vitamine A component and the much smaller amount of antioxidant, which is preferably also present, are dissolved in neutral oil, followed by sterile filtration. The sterile oil solution is then worked into the gel with stirring.

A comparable procedure is used when a preparation without gel basis, e.g. a drop solution is to be prepared.

The gel forming agents used according to this invention are preferably polyacrylic acids with a molecular weight of the order of approximately 3 to 5 million. Specifically preferred are the trade products such as Carbopol® polymeric acids as obtainable from B. F. Goodrich Chemicals Co. Carbopol 980 NF® is especially preferred. In the preparation, the concentration is approximately 0.2 weight-%.

The neutralization necessary for gel formation is customarily carried out using sterile diluted sodiumhydroxide solution, whereby 1-N sodiumhydroxide solution is specifically advantageous. However, also other inorganic bases or alkali carbonates, or organic bases such as amines, especially triethylamine and diisopropylamine can be used.

The gels thus obtained have viscosities in the range of approximately 2000 to 6000 mPa·s at 20° C.

The preserving agent which is generally used according to this invention, such as centrimid, benzalkoniumchloride or thiomersal, is used in the customary concentration, i.e.

approximately 0.01 weight-% in the case of centrimid. The isotoning agent, e.g. polyfunctional alcohols such as mannitol, dextrose, glycerol, propylene glycol or, especially preferred, sorbitol, are also used in customary concentrations. For sorbitol, a concentration of approximately 4.85 weight-% is specifically advantageous.

The invention will now be further explained on the basis of two examples:

EXAMPLE 1

A homogeneous suspension of 2000 kg polyacrylic acid (Carbopol 980 NF®) in approximately 375 kg water (pro injectionem) is introduced, through a fibre removal filter with a pore size of approximately 25 to 40 μm into a processing apparatus. This suspension is then autoclaved under stirring at 121° C. and 1 bar excess pressure for 20 minutes, and is then cooled to room temperature whereby ambient pressure is provided using a sterilized air filter.

Meanwhile, approximately 964 kg water (pro injectionem) are provided in a suitable vessel, and under stirring, 0.100 kg centrimid and then 48.510 kg sorbitol are dissolved therein. This solution is added to the already autoclaved polyacrylic acid suspension using a vapour sterilized membrane filter with a pore size of 0.2 μm, and nitrogen as the pressurizing gas. Subsequently, the apparatus is evacuated once or more to destroy any foam that may have formed.

Now, 0.832 kg sodiumhydroxide are dissolved in approximately 20 kg water (pro injectionem) under stirring and sterile conditions. The sodiumhydroxide is added by filtration through a vapour sterilized membrane filter to the centrimid/sorbitol/polyacrylic acid suspension, whereupon the remaining amount of water (pro injectionem) is added. The gel thus formed is worked by a homogenizer.

Then, the medium chain triglycerides are worked into the sterile gel, being added through a sterile filter with a pore size of 0.2 μm, followed by stirring until complete homogenization has been achieved. The pH value of the thus formed gel is determined, which should be 6 to 8 at 20° C. The osmolality of the inventive preparation is in the range of 260 to 320 mOsm/kg. The gel formed in this fashion is then filled into 5 g polyfoil tubes under aseptic conditions.

EXAMPLE 2

0.6 g vitamine A palmitate and 0.03 g vitamine E acetate are dissolved in 9.37 g neutral oil (Myritol 318®).

The solution is filtered through a 0.22 μm filter (Millipore®) so that it is sterile.

10 g of the neutral oil solution are added to 990 g gel prepared according to Example 1, and are worked into the gel using a wing stirrer. After 20 minutes of stirring the ready product is filled into 10 g polyfoil tubes. The gel corresponds to a content of 500 international units vitamine A per gramm preparation, at a 20% access.

COMPARATIVE EXAMPLE

A Carbopol gel is made according to Example 1; however, the medium chain triglyceride component is not provided.

Comparative Test

As according to Example 2, the gel of the Comparative Example is provided with a corresponding content of vitamine A palmitate.

Samples of this vitamine A preparation without triglyceride component are stored together with corresponding samples according to Example 2, under standard conditions. After a total of six months storage time, the vitamine A content in the comparative samples without triglyceride component has fallen by a total of 20%. In the samples according to Example 2, the vitamine A content is found-to be unchanged within the accuracy of determination.

What is claimed is:

1. A sterile ophthalmic drop preparation for the treatment of dry eye, comprising two phases, an aqueous phase and a liquid hydrophobic phase, wherein the preparation has the form of a gel, has a viscosity in the range of approximately 2000 to 6000 mpa·s at 20° C., and is essentially free from an emulgator substance.

2. The preparation according to claim 1, wherein the aqueous phase is a continuos phase, and the hydrophobic phase has the form of droplets dispersed therein.

3. The preparation according to claim 1, wherein the aqueous phase contains at least one polymeric gel-forming component.

4. The preparation according to claim 1, wherein the hydrophobic phase comprises an ophthalmically acceptable organic oil that stays dispersed as droplets in the aqueous phase without any emulgator substance.

5. The preparation according to claim 4, wherein the organic oil comprises at least one member selected from the group consisting of a fatty acid derivative, a triglyceride and a phthalic acid ester.

6. The preparation according to claim 5, wherein the organic oil comprises a medium-chain triglyceride mixture predominantly or completely composed of $C_8$–$C_{12}$ fatty acids.

7. Preparation according to claim 6, wherein the preparation comprises between 0.5 and 10 weight percent of the medium-chain triglyceride mixture.

8. Preparation according to claim 1, wherein the preparation has a pH value of 6 to 8.

9. Preparation according to claim 1, wherein the preparation comprises at least one ophthalmic active agent in a therapeutically effective amount.

10. Preparation according to claim 9, wherein the preparation comprises a vitamin A component.

11. Preparation according to claim 10, wherein the preparation further comprises an antioxidant.

12. Preparation according to claim 1, wherein the preparation comprises preserving agent and an isotonic agent.

13. Preparation according to claim 12, wherein the preserving agent comprises at least one member selected from the group consisting of centrimid, benzalkoniumchloride and thimerosal.

14. Preparation according to claim 12, wherein the isotonic agent comprises sorbitol.

15. A method for producing a preparation of claim 1, comprising providing a sterile hydrogel that has a continues aqueous phase, and dispersing homogeneously the hydrophobic phase therein.

16. The method according to claim 15, wherein the aqueous phase comprises a polyacrylic acid, said method further comprising reacting the polyacrylic acid with a base to form a gel by neutralization of carboxylic acid groups of the acid.

17. The method according to claim 16, further comprising homogeneously mixing an ophthalmically active agent into the preparation under aseptic conditions.

18. A method of treating dry eye comprising administering drops of the preparation of claim 1.

19. The preparation according to claim 1, wherein the polymeric gel-forming component comprises at least one member selected from the group consisting of a polyacrylic acid and a polymeric acrylic acid derivative, in an amount sufficient to provide gel properties to the preparation.

20. The preparation according to claim 19, wherein the preparation contains between 0.1 and 3 weight percent of polyacrylic acid.

* * * * *